(12) United States Patent
Ryan et al.

(10) Patent No.: US 10,563,146 B2
(45) Date of Patent: Feb. 18, 2020

(54) PREPARATION AND USE OF AMINOALKYLPHOSPHONIC ACID DILAKYL ESTER COMPOUNDS IN A LUBRICANT FOR ANTIWEAR, FRICTION REDUCTION, AND/OR MICROPITTING PREVENTION

(75) Inventors: Helen T. Ryan, London (GB); Bevin W. Parks-Lee, Midlothian, VA (US); Jeffrey J. Soden, Midlothian, VA (US); Stuart Wickson, Leeds (GB)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 13/606,208

(22) Filed: Sep. 7, 2012

(65) Prior Publication Data

US 2013/0072407 A1 Mar. 21, 2013

(30) Foreign Application Priority Data

Sep. 15, 2011 (EP) .................................... 11181490

(51) Int. Cl.
*C07F 9/6571* (2006.01)
*C10L 1/26* (2006.01)
*C10M 137/10* (2006.01)
*C10M 137/12* (2006.01)

(52) U.S. Cl.
CPC ................... *C10M 137/12* (2013.01)

(58) Field of Classification Search
CPC .......................... C10M 137/08; C10M 137/10
USPC .................................................. 508/435, 436
See application file for complete search history.

(56) References Cited

U.S. PATENT DOCUMENTS

| 2,635,112 A * | 4/1953 | Fields ........................... 558/135 |
| 3,076,010 A | 1/1963 | Beck et al. |
| 3,235,517 A * | 2/1966 | Beck et al. .................. 521/165 |
| 3,549,728 A | 12/1970 | Balde et al. |
| 4,052,487 A * | 10/1977 | Sturtz .................. C07F 9/4006 558/169 |
| 4,943,672 A | 7/1990 | Hamner et al. |

(Continued)

FOREIGN PATENT DOCUMENTS

CN 101993766 A 3/2011
DE 1232142 B1 1/1967

(Continued)

OTHER PUBLICATIONS

Alcon, Ribera, Galia, Cadiz, "Advanced Flame-Retardant Epoxy Resins From Phosphorus-Containing Diol," Journal of Polymer Science Part A: Polymer Chemistry, vol. 43, No. 16, Jan. 1, 2005, pp. 3510-3515.

(Continued)

*Primary Examiner* — Prem C Singh
*Assistant Examiner* — Francis C Campanell
(74) *Attorney, Agent, or Firm* — Barnes & Thornburg LLP

(57) ABSTRACT

In accordance with the disclosure, one aspect of the present application is directed to a lubricant additive composition. The lubricant additive composition includes a component or mixture of components selected from (a) an aminoalkylphosphonic acid dialkyl ester; (b) a cyclized product of an aminoalkylphosphonic acid dialkyl ester; and a mixture of (a) and (b). Preparation and use of the additive composition in a lubricant for antiwear and/or friction reduction are also disclosed.

16 Claims, 2 Drawing Sheets

(56) References Cited

U.S. PATENT DOCUMENTS

| | | | |
|---|---|---|---|
| 5,124,055 A * | 6/1992 | Perozzi | C10M 135/06 252/48.6 |
| 5,882,505 A | 3/1999 | Wittenbrink et al. | |
| 6,013,171 A | 1/2000 | Cook et al. | |
| 6,080,301 A | 6/2000 | Berlowitz et al. | |
| 6,096,940 A | 8/2000 | Wittenbrink et al. | |
| 6,103,099 A | 8/2000 | Wittenbrink et al. | |
| 6,165,949 A | 12/2000 | Berlowitz et al. | |
| 6,180,575 B1 | 1/2001 | Nipe | |
| 7,176,168 B2 * | 2/2007 | Vann et al. | 508/253 |

FOREIGN PATENT DOCUMENTS

| | | |
|---|---|---|
| EP | 0608018 A1 | 7/1994 |
| GB | 1183471 | 3/1970 |

OTHER PUBLICATIONS

Ellis K. Fields, "The Synthesis of Esters of Stubstituted Amino Phosphonic Acids," Journal of the American Chemical Society, vol. 74, No. 6, Mar. 20, 1952, pp. 1528-1531.
Office Action dated May 5, 2019 for corresponding Chinese Application No. 201610651741.5 (English translation included).

* cited by examiner

PREPARATION AND USE OF AMINOALKYLPHOSPHONIC ACID DIALKYL ESTER COMPOUNDS IN A LUBRICANT FOR ANTIWEAR, FRICTION REDUCTION, AND/OR MICROPITTING PREVENTION

TECHNICAL FIELD

The present application is directed to compounds, lubricant additives and compositions, and methods for using aminoalkylphosphonic acid dialkyl ester compounds as antiwear additives and/or friction reducing agents.

BACKGROUND

Antiwear additives are commonly used in lubricant compositions to reduce, and preferably, prevent wear of surfaces. If such antiwear additives provided additional benefits to lubricant compositions, e.g., performing more than one function by their presence, these additives could simplify formulations, contain costs, preserve resources, and potentially provide other advantages. For example, an additional desired and useful property of antiwear additives is providing reduced friction between surfaces.

FIGURES

SUMMARY

Figure 1:
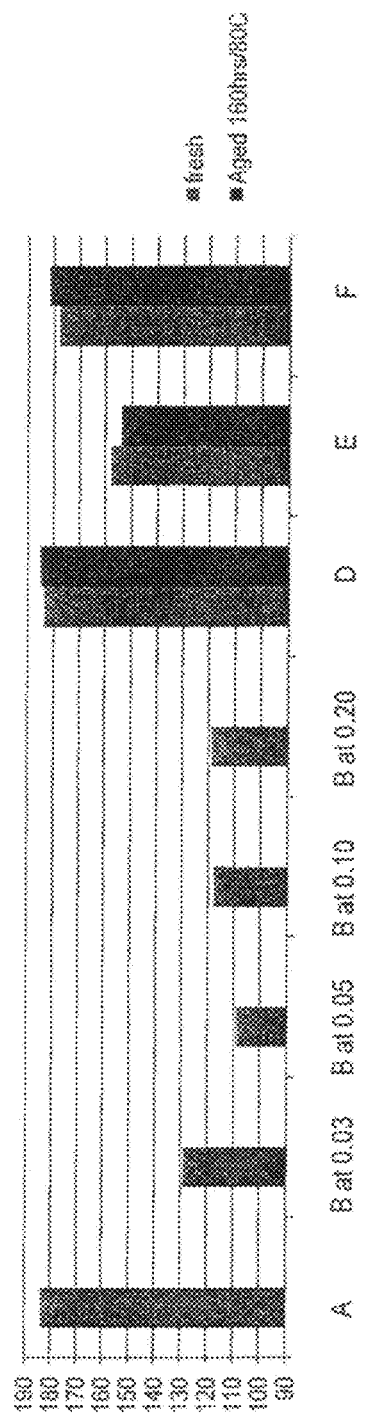
FIG. 1 is a bar graph showing wear test data generated by a HFRR Test Rig.

The present disclosure describes a novel lubricant additive composition for use as antiwear additives and/or friction reducing agents. They may be capable of being used at relatively low treatment rates, and they may meet the anti-wear requirements of Original Equipment Manufacturers (OEMs) worldwide, including in the U.S., Europe, Asia-Pacific, and Asia, as well as service fill applications.

An embodiment of the present disclosure describes a novel lubricant additive composition that includes a component or mixture of components selected from (a) an aminoalkylphosphonic acid dialkyl ester; (b) a cyclized product of an aminoalkylphosphonic acid dialkyl ester; and a mixture of (a) and (b).

In some embodiments, the aminoalkylphosphonic acid dialkyl ester comprises the formula (I):

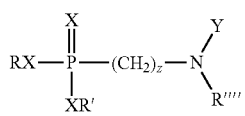

(I)

wherein each X is independently selected from sulfur and oxygen, R and R' are independently selected from hydrocarbyl radicals containing from about 2 to about 20 carbon atoms; Y is selected from an alkyl group having from about 1 to about 30 carbon atoms, an alcohol having from about 1 to about 30 carbon atoms, and the group $R''O(R'''O)_n$—H; R'' and R''' are independently divalent aliphatic hydrocarbon radicals containing from about 1 to about 4 carbon atoms, n is an integer from 0 to 20; and R'''' is selected from hydrogen, an alkyl group having from about 1 to about 30 carbon atoms, an alcohol having from about 1 to about 30 carbon atoms, and the group $R''O(R'''O)_n$—H; In some embodiments, the aminoalkylphosphonic acid dialkyl ester comprises N,N-bis(2-hydroxylethyl)aminomethylphosphonic acid diethyl ester having the formula (II):

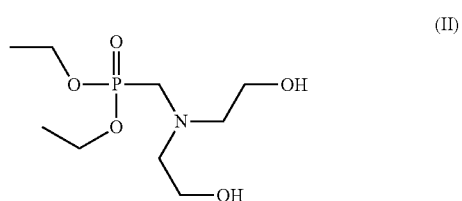 [SMILES: CCOP(=O)(CN(CCO)CCO)OCC]

(II)

In some embodiments, the cyclized product of the aminoalkylphosphonic acid dialkyl ester comprises the cyclized product of N,N-bis(2-hydroxylethyl)aminomethylphosphonic acid diethyl ester having the formula (III):

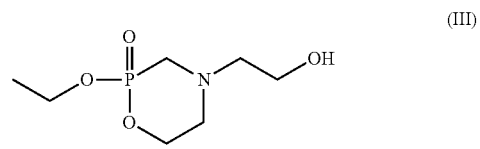

(III)

In some embodiments, the dialkyl (hydroxyalkyl)phosphonate comprises diethyl (hydroxymethyl)phosphonate having the formula (IV):

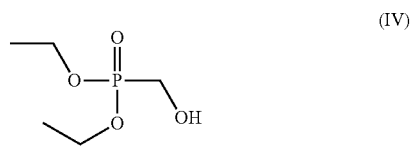

(IV)

In some embodiments, the aminoalkylphosphonic acid dialkyl ester is present in an amount of greater than about 50 wt % based on the total weight percent of the additive composition. In some embodiments, the cyclized product of aminoalkylphosphonic acid dialkyl ester is present in an amount of greater than about 20 wt % based on the total weight percent of the additive composition. In some embodiments, the dialkyl (hydroxyalkyl)phosphonate is present in an amount of less than about 20 wt %, but not 0 wt %, based on the total weight percent of the additive composition.

In another embodiment, a lubricant composition comprises a base oil and the additive composition described herein.

In some embodiments, the additive composition is present in an amount of greater than about 0.03 wt % in the lubricant composition.

In some embodiments, the additive composition is present in an amount of greater than about 0.05 wt % in the lubricant composition.

In another embodiment, a hydraulic fluid composition comprises a base oil and the additive composition described herein.

In another embodiment, a method for providing antiwear protection to a lubricated surface, comprises: lubricating a surface with a lubricant composition described herein.

In another embodiment, a method for reducing friction between lubricated surfaces, comprises: lubricating a surface with a lubricant composition described herein.

The method for providing antiwear protection to a lubricated surface may improve antiwear protection relative to a lubricant composition free of the lubricant additive composition.

The method for reducing friction between lubricated surfaces may improve antiwear protection relative to a lubricant composition free of the lubricant additive composition.

In another embodiment, a process for preparing an aminoalkylphosphonic acid dialkyl ester compound, includes reacting together a dialkyl phosphite, an aldehyde, and a dialkanolamine.

In some embodiments, the dialkyl phosphite is diethyl phosphite.

In some embodiments, the aldehyde is formaldehyde.

In some embodiments, the dialkanolamine is diethanolamine.

In some embodiments, the dialkyl phosphite comprises a member of the group selected from a di-butyl phosphite, a di-2-ethylhexyl phosphite, a di-phenyl phosphite, and a di-oleyl phosphite.

In another embodiment, a process for preparing an aminoalkylphosphonic acid dialkyl ester compound, includes reacting together a dialkyl phosphite, an aldehyde, and a dialkylamine.

In some embodiments, the dialkylamine comprises a member of the group selected from a diethylamine, a dipropylamine, and a dioleylamine.

In another embodiment, a process for preparing an aminoalkylphosphonic acid dialkyl ester compound, includes reacting together a dialkyl phosphite, an aldehyde, and bis(2-ethoxyethyl)amine.

The term "a mixture of components" is used to describe the mixture or combination of (a) an aminoalkylphosphonic acid dialkyl ester and (b) a cyclized product of an aminoalkylphosphonic acid dialkyl ester. Optionally, the mixture may also include (c) a dialkyl (hydroxyalkyl)phosphonate.

A mixture of the components described herein may be formed separately and then added to a lubricant or additive composition. Alternatively, a mixture of the components described herein may be formed when they are blended, mixed, and/or reacted with other components to form the lubricant or additive composition.

In an aspect, a mixture of components described herein may be present in a lubricant composition in any amount effective to provide enhanced antiwear performance and/or friction reduction on metal surfaces. For example, the mixture may be present in an amount ranging up to about 10 wt. % but not 0 wt. %, for example up to about 0.1 wt. % but not 0 wt. %, and as a another example up to about 0.05 wt. % but not 0 wt %, and as an even further example, up to about 0.03 wt % but not 0 wt %, relative to the total weight of the lubricant composition.

As used herein, the term "alkyl," as well as the alkyl moieties of other groups referred herein (e.g., alkoxy), may be linear or branched (such as methyl, ethyl, n-propyl, isopropyl, n-butyl, iso-butyl, secondary-butyl, tertiary-butyl); optionally substituted by 1 to 3 suitable substituents as defined above such as fluoro, chloro, trifluoromethyl, ($C_1$-$C_6$)alkoxy, ($C_6$-$C_{10}$)aryloxy, trifluoromethoxy, difluoromethoxy or ($C_1$-$C_6$)alkyl. The phrase "each of said alkyl" as used herein refers to any of the preceding alkyl moieties within a group such as alkoxy, alkenyl or alkylamino.

As used herein, the terms "oil composition," "lubrication composition," "lubricating oil composition," "lubricating oil," "lubricant composition," "fully formulated lubricant composition," and "lubricant" are considered synonymous, fully interchangeable terminology referring to the finished lubrication product comprising a major amount of a base oil plus a minor amount of an additive composition.

As used herein, the terms "additive package," "additive concentrate," and "additive composition" are considered synonymous, fully interchangeable terminology referring to the portion of the lubricating composition excluding the major amount of base oil stock mixture.

As used herein, the terms "agent" and "additive" are considered synonymous, fully interchangeable terminology referring to any single functional component of a lubricating composition, excluding the major amount of base oil stock mixture.

Additional objects and advantages of the disclosure will be set forth in part in the description which follows, and/or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

DETAILED DESCRIPTION

The mixture of components disclosed herein may be prepared using the example synthetic route outlined in the following scheme:

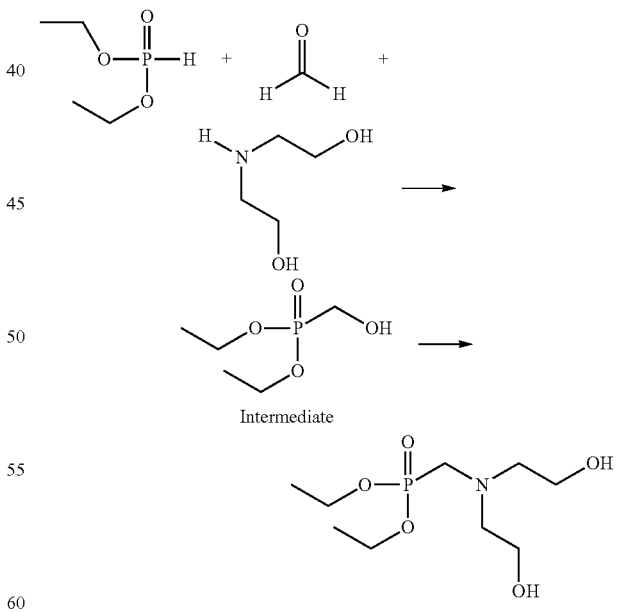

If diethyl phosphite, formaldehyde, and an amine are reacted, the resulting product is a phosphonate product (with water being a by-product that is not shown in the scheme). There is an intermediate phosphonate that is produced from this process, and so the resulting product may include this intermediate.

A cyclized product of the resulting product is produced from the following rearrangement:

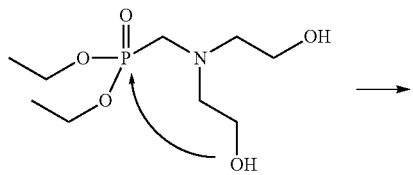

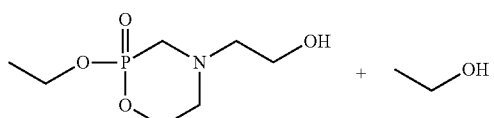

The resulting product from the above scheme includes greater than about 50 wt % N,N-bis(2-hydroxylethyl)aminomethylphosphonic acid diethyl ester, greater than about 20 wt % cyclized product of N,N-bis(2-hydroxylethyl)aminomethylphosphonic acid diethyl ester, and less than about 20 wt %, but not 0 wt %, diethyl (hydroxymethyl)phosphonate. As a further example, the resulting product may comprise about 58 wt % N,N-bis(2-hydroxylethyl)aminomethylphosphonic acid diethyl ester, about 26 wt % cyclized product of N,N-bis(2-hydroxylethyl)aminomethylphosphonic acid diethyl ester, and less than about 16 wt % diethyl (hydroxymethyl)phosphonate.

The resulting product may have a TBN of about 150 mg KOH/g to about 300 mg KOH/g, a TAN of about 10 mg KOH/g to about 30 mg KOH/g, and a KV40 of about 50 to about 75. As a further example, the resulting product may have a TBN of about 214 mg KOH/g, a TAN of about 21 mg KOH/g, and a KV40 of about 62.58.

Phosphoramides, esters, and amine derivatives of oxy- and thio-alkyl phosphorus acids with (1) oxyalkylated amines, (2) polyamines, and (3) polyhydric alcohols may be formed, for example, by reacting the amine or alcohol with an acid chloride of a dialkyl phosphorus acid of the formula:

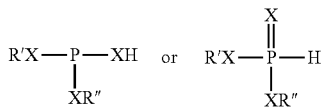

where R' and R" are independently selected from hydrocarbyl radicals containing from about 2 to 20 carbons and X is selected from oxygen and sulfur including various combinations thereof. The hydrocarbyl group may be selected from $C_8$-$C_{20}$ alkyl or alkenyl to provide oil solubility. As in the case of the alkoxylated amines, the reaction of the acids and oxyalkylated amines forms not only amides but esters and ester-amides. The dialkyl phosphorus acids may be prepared, for example, by reacting one or more alcohols, containing about 4 to 20 carbons, such as n-butanol, isobutanol, t-butanol, 2-butanol, pentanol, hexanol, cyclohexanol, 2-ethylhexanol, 1-decanol, 1-dodecanol, cetyl alcohol, and stearyl alcohol with an inorganic phosphorus pentasulfide. The acid chlorides may be prepared by reaction of the acid with chlorine, for example:

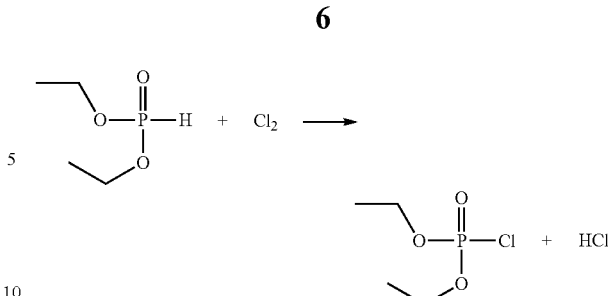

The amine derivatives which may also be considered as being esters of the phosphorus acid may be prepared by reacting a dialkylphosphite with formaldehyde and a dialkanol amine, for example, as follows:

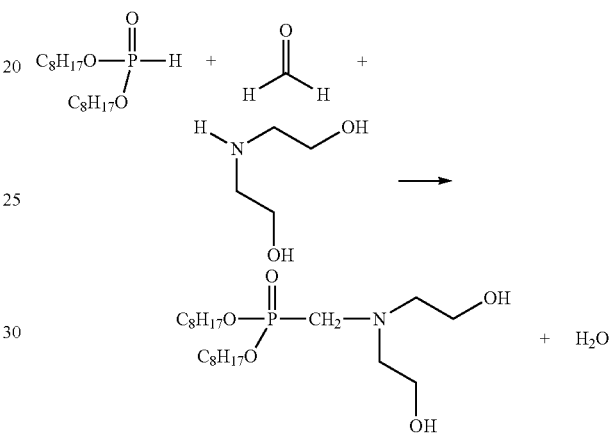

In some embodiments, the alcohol of dialkyanolamine is replaced by an alkyl. So that dialkylamine is used. For example, di-ethanolamine may be replaced with one or more of di-ethylamine, di-propylamine, di-oleylamine, or the conversion of the hydroxyl groups on the di-ethanolamine to an ether. This product may be made by converting the —OH groups of diethanolamine in step one of the synthesis to ethers. For example, converting diethanolamine to bis(2-ethoxyethyl)amine. The two ether ends may inhibit the cyclization reaction and enhance solubility.

In some embodiments, the R groups in the phosphite may be di-butyl, di-2-ethylhexyl, di-phenyl, or di-oleyl. A phosphite other than ethyl phosphite in the second step of the synthesis may be used. The intention is to have R-groups that are bulky enough to sterically hinder the cyclization reaction. For example, 2-ethylhexyl phosphite or an alkyl group branched at the C directly attached to the O. As a further example, diphenyl phosphite may be used.

In some embodiments, the methyl group bonded between phosphorus and nitrogen may be an alkyl chain having from 1 to about 30 carbon atoms. This is depicted below where z is 1-30.

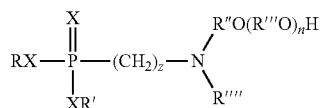

Base Oil

The lubricating compositions disclosed herein may comprise a base oil. Base oils suitable for use in formulating the disclosed compositions may be selected from, for example, synthetic or mineral oils, or mixtures thereof.

The base oil may be present in a major amount, wherein "major amount" is understood to mean greater than or equal to 50% by weight of the lubricant composition, such as from about 80% to about 98% by weight of the lubricant composition. The base oil typically has a viscosity of, for example, from about 2 to about 15 cSt and, as a further example, from about 2 to about 10 cSt at 100° C.

Non-limiting examples of mineral oils suitable as base oils include animal oils and vegetable oils (e.g., castor oil, lard oil) as well as other mineral lubricating oils such as liquid petroleum oils and solvent treated or acid-treated mineral lubricating oils of the paraffinic, naphthenic or mixed paraffinic-naphthenic types. Oils derived from coal or shale are also suitable. Further, oils derived from a gas-to-liquid process are also suitable.

Non-limiting examples of synthetic oils include hydrocarbon oils such as polymerized and interpolymerized olefins (e.g., polybutylenes, polypropylenes, propylene isobutylene copolymers, etc.); polyalphaolefins such as poly(1-hexenes), poly(1-octenes), poly(1-decenes), etc. and mixtures thereof; alkylbenzenes (e.g., dodecylbenzenes, tetradecylbenzenes, di-nonylbenzenes, di-(2-ethylhexyl)benzenes, etc.); polyphenyls (e.g., biphenyls, terphenyl, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic oils that may be used. Such oils are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500-1000, diethyl ether of polypropylene glycol having a molecular weight of about 1000-1500, etc.) or mono- and polycarboxylic esters thereof, for example, the acetic acid esters, mixed $C_{3-8}$ fatty acid esters, or the $C_{13}$ Oxo acid diester of tetraethylene glycol.

Another class of synthetic oils that may be used includes the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_{5-12}$ monocarboxylic acids and polyols and polyol ethers such as neopentyl glycol, trimethylol propane, pentaerythritol, dipentaerythritol, tripentaerythritol, etc.

Hence, the base oil used to make the compositions as described herein may be selected from any of the base oils in Groups I-V as specified in the American Petroleum Institute (API) Base Oil Interchangeability Guidelines. Such base oil groups are as follows:

Group I contain less than 90% saturates and/or greater than 0.03% sulfur and have a viscosity index greater than or equal to 80 and less than 120; Group II contain greater than or equal to 90% saturates and less than or equal to 0.03% sulfur and have a viscosity index greater than or equal to 80 and less than 120; Group III contain greater than or equal to 90% saturates and less than or equal to 0.03% sulfur and have a viscosity index greater than or equal to 120; Group IV are polyalphaolefins (PAO); and Group V include all other basestocks not included in Group I, II, III or IV.

The test methods used in defining the above groups are ASTM D2007 for saturates; ASTM D2270 for viscosity index; and one of ASTM D2622, 4294, 4927 and 3120 for sulfur.

Group IV basestocks, i.e. polyalphaolefins (PAO) include hydrogenated oligomers of an alpha-olefin, the most important methods of oligomerization being free radical processes, Ziegler catalysis, and cationic, Friedel-Crafts catalysis.

The polyalphaolefins typically have viscosities in the range of 2 to 100 cSt at 100° C., for example 4 to 8 cSt at 100° C. They can, for example, be oligomers of branched or straight chain alpha-olefins having from about 2 to about 30 carbon atoms; non-limiting examples include polypropenes, polyisobutenes, poly(1-butenes), poly(1-hexenes), poly(1-octenes) and poly(1-decenes). Included are homopolymers, interpolymers and mixtures.

Regarding the balance of the basestock referred to above, a "Group I basestock" also includes a Group I basestock with which basestock(s) from one or more other groups may be admixed, provided that the resulting admixture has characteristics falling within those specified above for Group I basestocks.

Exemplary basestocks include Group I basestocks and mixtures of Group II basestocks with Group I basestock.

Basestocks suitable for use herein may be made using a variety of different processes including but not limited to distillation, solvent refining, hydrogen processing, oligomerization, esterification, and re-refining.

The base oil may be an oil derived from Fischer-Tropsch synthesized hydrocarbons. Fischer-Tropsch synthesized hydrocarbons may be made from synthesis gas containing $H_2$ and CO using a Fischer-Tropsch catalyst. Such hydrocarbons typically require further processing in order to be useful as the base oil. For example, the hydrocarbons may be hydroisomerized using processes disclosed in U.S. Pat. No. 6,103,099 or 6,180,575; hydrocracked and hydroisomerized using processes disclosed in U.S. Pat. No. 4,943,672 or 6,096,940; dewaxed using processes disclosed in U.S. Pat. No. 5,882,505; or hydroisomerized and dewaxed using processes disclosed in U.S. Pat. Nos. 6,013,171; 6,080,301; or 6,165,949.

Unrefined, refined and rerefined oils, either mineral or synthetic (as well as mixtures of two or more of any of these) of the type disclosed hereinabove may be used in the base oils. Unrefined oils are those obtained directly from a mineral or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils, where the processes are applied to refined oils which have been already used in service. Such rerefined oils are also known as reclaimed or reprocessed oils and often are additionally processed by techniques directed to removal of spent additives, contaminants, and oil breakdown products.

The lubricant compositions of the present application may be used in any industrial application or fluid.

Optional Additive Components

In another aspect of the present disclosure, the presently disclosed mixture of components may be formulated into an additive composition and blended with a base oil to obtain a lubricating fluid. Such a fluid may be formulated optionally with one or more selected ingredients and additives that include, without limitation, those described hereinbelow. Such additives may include, but are not limited to, antifoamants (foam inhibitors), antioxidants, anti-rust additives, antiwear additives, colorants, corrosion inhibitors, dispersants, extreme pressure agents, friction modifiers, metal deactivators, detergents, organic phosphorus compounds, pour point depressants, seal swell agents, demulsifiers, polyalkylene glycol components, and/or viscosity index improvers. The supplemental additives include those that are commercially available.

In selecting any of the optional additives, it may be important to ensure that the selected component(s) may be soluble or stably dispersible in the additive package and the finished lubricant composition, and may be compatible with the other components of the composition. By preference, a person skilled in the art may be expected to choose an additional optional additive or combination of additives, amounts thereof, such that the performance properties of the composition, such as the improved extreme pressure or thermal stability performance, among other properties, needed or desired, as applicable, in the overall finished composition, may not be substantially adversely affected.

In general, the ancillary additive components may be employed in the lubricating oil in minor amounts sufficient to improve the performance characteristics and properties of the base fluid. The amounts may thus vary in accordance with such factors as the viscosity characteristics of the base fluid employed, the viscosity characteristics desired in the finished fluid, the service conditions for which the finished fluid is intended, and the performance characteristics desired in the finished fluid.

It will be appreciated that the individual components employed may be separately blended into the base fluid or may be blended therein in various sub-combinations, if desired. Ordinarily, the particular sequence of such blending steps is not crucial. Moreover, such components may be blended in the form of separate solutions in a diluent. It may be preferable, however, to blend the additive components used in the form of a concentrate, as this simplifies the blending operations, reduces the likelihood of blending errors, and takes advantage of the compatibility and solubility characteristics afforded by the overall concentrate.

Additive concentrates may thus be formulated to contain all of the additive components and if desired, some of the base oil component, in amounts proportioned to yield finished fluid blends consistent with the concentrations described above. In most cases, the additive concentrate will contain one or more diluents such as light mineral oils, to facilitate handling and blending of the concentrate. Thus concentrates containing up to about 50 wt. % of one or more diluents or solvents may be used, provided the solvents are not present in amounts that interfere with the low and high temperature and flash point characteristics and the performance of the finished power transmission fluid composition. In this regard, the additive components used pursuant to this disclosure may be selected and proportioned such that an additive concentrate or package formulated from such components will have a flash point of about 170° C. or above, using the ASTM D-92 test procedure.

The following Examples are offered to specifically illustrate this invention. These Examples and illustrations are not to be construed in any way as limiting the scope of this invention.

EXAMPLES

The additive composition described herein was tested using a High Frequency Reciprocating Rig ("HFRR") Test and Apparatus. HFRR Testing was conducted using the following conditions on fresh and aged reference oils of known performance. Aged oils were aged at 90° C. for 80 hours, 160 hours, and up to 560 hours.

Figure 2:
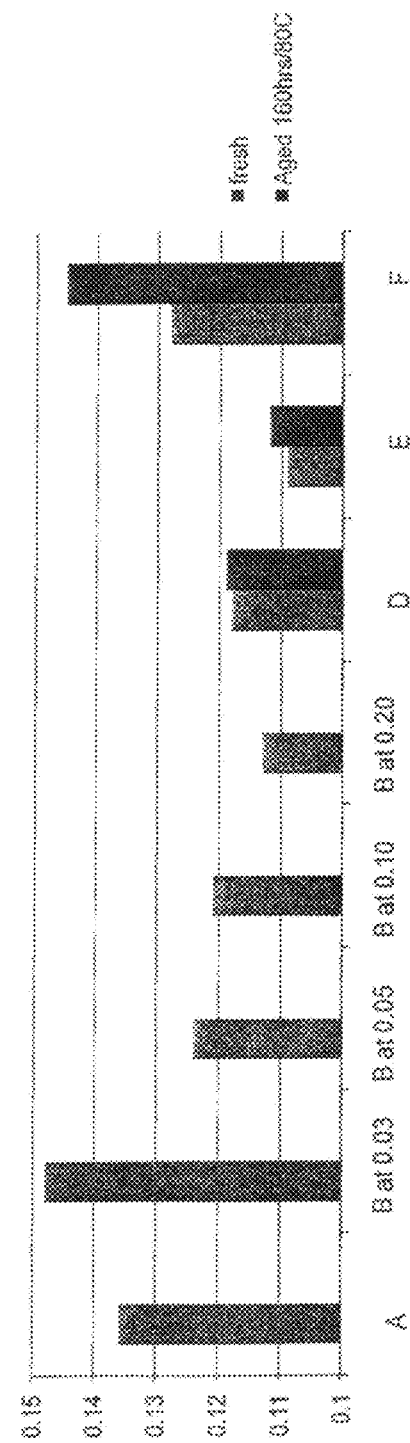
FIG. 2 is a bar graph showing friction test data generated by a HFRR Test Rig.

For the friction test results in FIG. 2, friction values comparable to the passing reference oils was desired. For the wear test results in FIGS. 1 and 3, a value less than 180 is indicative of expected good wear performance in a FAG FE8 test. The test conditions for the FIG. 2 friction testing were 70° C., 4N, 20 Hz, and 1 mm for steel-on-steel for 3 minutes. The test conditions for the FIG. 1 wear testing were 70° C., 100° C., and 130° C., 4N, and 20 Hz/mm on steel-on-steel for 9 minutes. The test conditions for the FIG. 3 wear testing were 80° C., 4N, 20 Hz, and 1 mm for 3 minutes on steel-on-steel.

In the figures, Fluid A contained base oil only (ISO 100VG). Fluid B contained components according to the present disclosure, specifically, a combination of about 58 wt % N,N-bis(2-hydroxylethyl)aminomethylphosphonic acid diethyl ester (formula V below), about 26% cyclized product of N,N-bis(2-hydroxylethyl)aminomethylphosphonic acid diethyl ester, and balance diethyl (hydroxymethyl) phosphonate. Fluid C contained a passing FAG FE8 Round Robin Oil. Fluid D contained an Afton FAG FE8 Round Robin Oil.

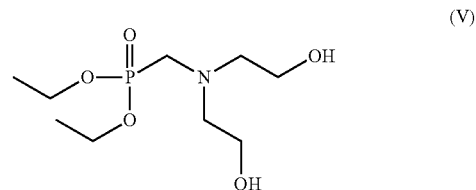

(V)

Figure 3:
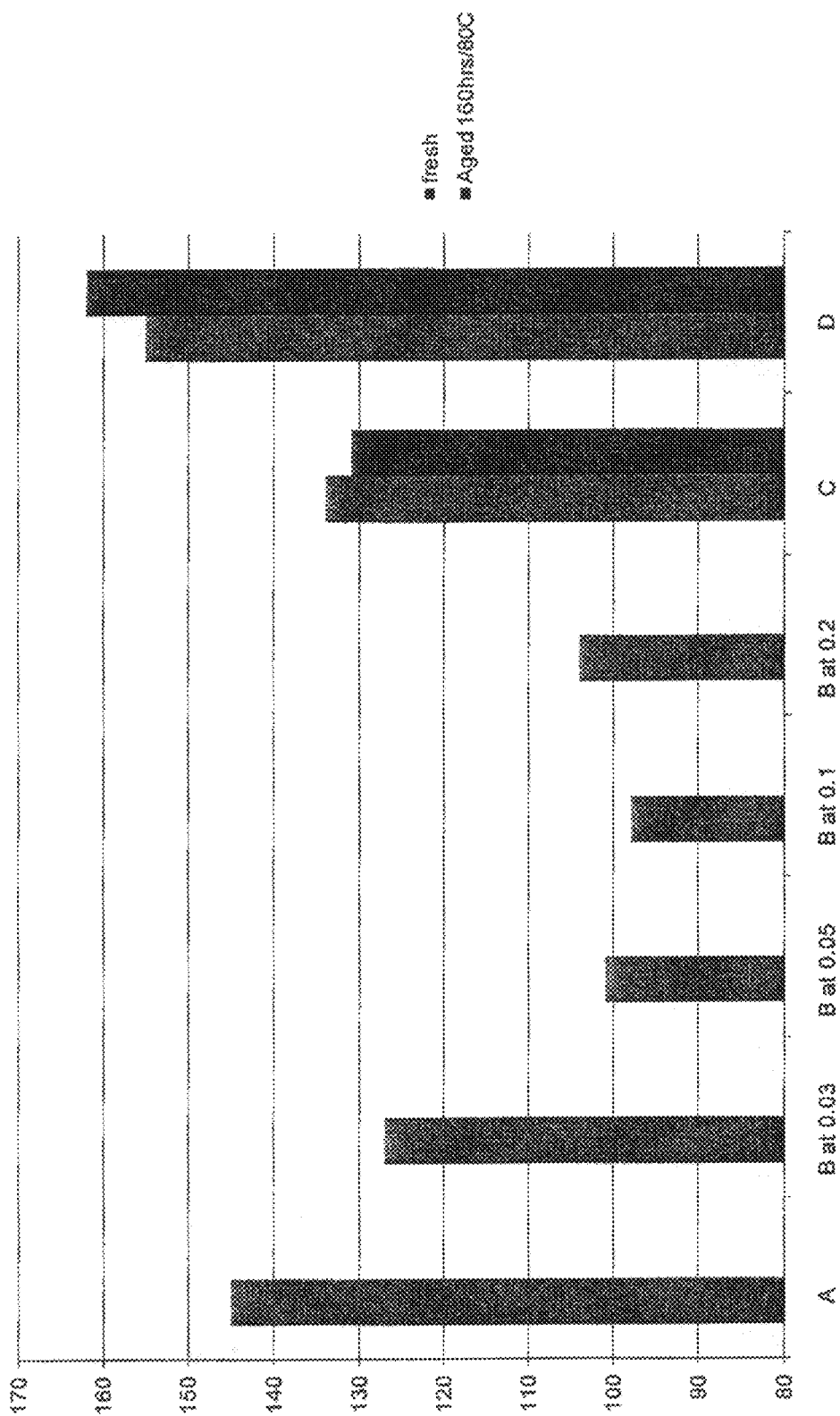
FIG. 3 is a bar graph showing wear test data generated by a HFRR Test Rig.

In FIGS. 1-3, it is evidenced that compositions according to the present disclosure provide improved wear protection and reduction in friction. As the level of the component increases, the wear protection improves as does the friction reduction. At low levels of 0.03 wt %, wear protection is provided but the friction is higher. This indicates that when the present composition is used with other antiwear agents, the lower level might allow other effective antiwear agents to the lubricated surface. In FIG. 3, it is apparent that when Component B was present, the friction was reduced from 0.163 to 0.119 as the amount of Component B increased. High friction is attainable with very low levels of Component B.

Additional variations of formula I were tested. The five variations were N,N-bis(2-ethyl)aminomethane phosphonic acid diethyl ester (formula VI); N,N-bis(2-butyl)aminomethane phosphonic acid diethyl ester (formula VII); N,N-bis(2-ethyl)aminomethane phosphonic acid dibutyl ester (formula VIII); N,N-bis(2-butyl)aminomethane phosphonic acid dibutyl ester (formula IX); and N,N-bis(2-hydroxyethyl)aminomethane phosphonic acid dibutyl ester (formula X).

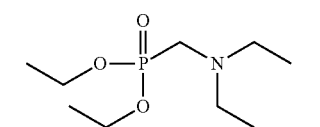
(VI)

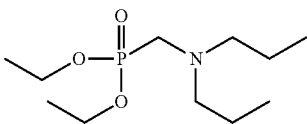
(VII)

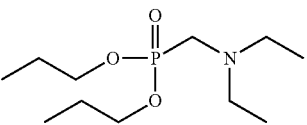
(VIII)

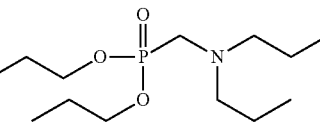
(IX)

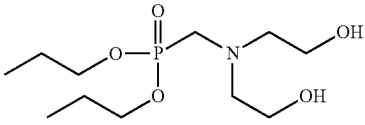
(X)

The fluids were tested in a lubricant formulation, wherein the additive treat rate was 0.2 wt % for each variant based on the weight percent in the lubricant formulation. The fluids were tested using the HFRR Test Rig for wear and friction performance. The HFRR test conditions included 70° C., 100° C., and 130° C., 400 grams, 20 Hz, 1 mm, for 9 minutes and also 80° C., 400 grams, 20 Hz, 1 mm, for 3 minutes.

Fluids including formula VI, VII, VIII, and IX were tested. Formula X was immiscible in both Group I and Group II base oils and was not tested. Formula V was also tested for comparison purposes. Testing was done using both Group I and Group II base oils on both new and aged fluids. The test results are provided in Tables I-IV below.

TABLE I

Group I, Fresh Oils

| HFRR | Formula V | Formula VI | Formula VII | Formula VIII | Formula IX |
|---|---|---|---|---|---|
| Friction @ 70° C. | 0.116 | 0.15 | 0.15 | 0.15 | 0.14 |
| Friction @ 100° C. | 0.138 | 0.14 | 0.16 | 0.12 | 0.13 |
| Friction @ 130° C. | 0.156 | 0.15 | 0.17 | 0.13 | 0.13 |
| Wear Scar in μm | 135.5 | 180 | 179 | 155.5 | 169.5 |
| Friction @ 80° C. | 0.138 | 0.15 | 0.16 | 0.14 | 0.14 |
| Wear Scar in μm | 124 | 143.5 | 142.5 | 129.5 | 132 |

TABLE II

Group I, Aged Oils

| HFRR | Formula V | Formula VI | Formula VII | Formula VIII | Formula IX |
|---|---|---|---|---|---|
| Friction @ 70° C. | 0.120 | 0.15 | 0.15 | 0.14 | 0.14 |
| Friction @ 100° C. | 0.129 | 0.16 | 0.16 | 0.15 | 0.13 |
| Friction @ 130° C. | 0.131 | 0.17 | 0.17 | 0.14 | 0.12 |
| Wear Scar in μm | 119.5 | 189.5 | 199.5 | 185 | 193.5 |
| Friction @ 80° C. | 0.121 | 0.15 | 0.15 | 0.15 | 0.14 |
| Wear Scar in μm | 119 | 151.5 | 166.5 | 155.5 | 156.5 |

TABLE III

Group II, Fresh Oils

| HFRR | Formula V | Formula VI | Formula VII | Formula VIII | Formula IX |
|---|---|---|---|---|---|
| Friction @ 70° C. | 0.10 | 0.15 | 0.15 | 0.12 | 0.14 |
| Friction @ 100° C. | 0.11 | 0.14 | 0.15 | 0.11 | 0.13 |
| Friction @ 130° C. | 0.12 | 0.14 | 0.12 | 0.1 | 0.13 |
| Wear Scar in μm | 140.5 | 176.5 | 171.5 | 159 | 174.5 |
| Friction @ 80° C. | — | 0.15 | 0.15 | 0.12 | 0.13 |
| Wear Scar in μm | — | 125.5 | 141 | 137.5 | 166 |

TABLE IV

Group II, Aged Oils

| HFRR | Formula V | Formula VI | Formula VII | Formula VIII | Formula IX |
|---|---|---|---|---|---|
| Friction @ 70° C. | 0.12 | 0.15 | 0.14 | 0.11 | 0.13 |
| Friction @ 100° C. | 0.16 | 0.12 | 0.14 | 0.1 | 0.13 |
| Friction @ 130° C. | 0.14 | 0.13 | 0.13 | 0.08 | 0.12 |
| Wear Scar in μm | 166.5 | 171 | 176.5 | 154 | 171.5 |
| Friction @ 80° C. | — | 0.15 | 0.15 | 0.13 | 0.13 |
| Wear Scar in μm | — | 152 | 134.5 | 136.5 | 156 |

TABLE V

Formula V, Group I, Fresh Oils

| HFRR | 0.00 wt % Formula V | 0.025 wt % Formula V | 0.05 wt % Formula V | 0.10 wt % Formula V | 0.20 wt % Formula V |
|---|---|---|---|---|---|
| Friction @ 70° C. | 0.136 | 0.148 | 0.122 | 0.121 | 0.113 |
| Friction @ 100° C. | 0.153 | 0.134 | 0.124 | 0.122 | 0.113 |
| Friction @ 130° C. | 0.152 | 0.119 | 0.114 | 0.102 | 0.103 |
| Wear Scar in μm | 184 | 129 | 109 | 118 | 119 |
| Friction @ 80° C. | 0.143 | 0.163 | 0.135 | 0.117 | 0.119 |
| Wear Scar in μm | 145 | 127 | 101 | 97.5 | 104 |

TABLE VI

Formula V, Group I, Aged Oils

| HFRR | 0.00 wt % Formula V | 0.025 wt % Formula V | 0.05 wt % Formula V | 0.10 wt % Formula V | 0.20 wt % Formula V |
|---|---|---|---|---|---|
| Friction @ 70° C. | — | 0.142 | 0.126 | 0.12 | 0.111 |
| Friction @ 100° C. | — | 0.157 | 0.133 | 0.118 | 0.121 |
| Friction @ 130° C. | — | 0.136 | 0.116 | 0.112 | 0.117 |
| Wear Scar in μm | — | 163 | 156 | 123 | 102 |

TABLE VI-continued

Formula V, Group I, Aged Oils

| HFRR | 0.00 wt % Formula V | 0.025 wt % Formula V | 0.05 wt % Formula V | 0.10 wt % Formula V | 0.20 wt % Formula V |
|---|---|---|---|---|---|
| Friction @ 80° C. | — | 0.149 | 0.13 | 0.121 | 0.117 |
| Wear Scar in μm | — | 151 | 109 | 96 | 93 |

Tables V and VI show friction and wear scar results for formulations containing a Group I base oil alone and with treats of Formula V at 0.025 wt %, 0.05 wt %, 0.10 wt %, and 0.20 wt %. The data generally shows that wear and friction both improve as the treat rate of Formula V increases.

Additional variants include but are not limited to bulky alkyl phosphite variations shown below as formulae XI and XII and an ether variation shown below as formula XIII.

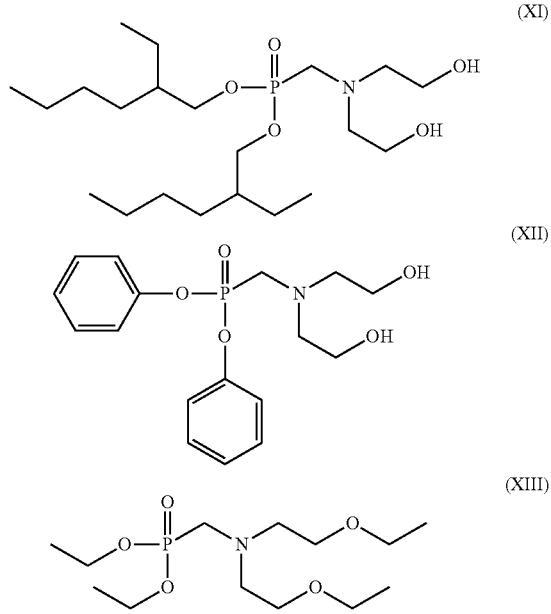

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," include plural referents unless expressly and unequivocally limited to one referent. Thus, for example, reference to "an acid" includes two or more different acids. As used herein, the term "include" and its grammatical variants are intended to be non-limiting, such that recitation of items in a list is not to the exclusion of other like items that may be substituted or added to the listed items.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A lubricant additive composition comprising:
   a component or mixture of components selected from the group consisting of:
   (a) an aminoalkylphosphonic acid dialkyl ester;
   (b) a cyclized product of an aminoalkylphosphonic acid dialkyl ester; and
   a mixture of (a) and (b); and
   at least one diluent oil,
   wherein the aminoalkylphosphonic acid dialkyl ester is a compound of formula (I):

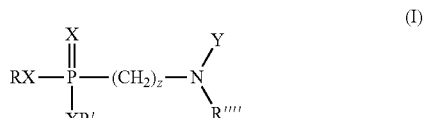

wherein each X is independently selected from sulfur and oxygen;
   wherein z is 1 to 30;
   wherein R and R' are independently selected from hydrocarbyl radicals containing 2 carbon atoms;
   wherein Y is selected from an alkyl group having from about 1 to about 30 carbon atoms, an alcohol having from about 1 to about 30 carbon atoms, and the group R"O(R'''O)$_n$—H, wherein R" and R''' are independently divalent aliphatic hydrocarbon radicals containing from about 1 to about 4 carbon atoms and n is an integer from 0 to 20; and
   wherein R"" is selected from hydrogen, an alkyl group having from about 1 to about 30 carbon atoms, an alcohol having from about 1 to about 30 carbon atoms, and the group R"O(R'''O)$_n$H, wherein R" and R''' are independently divalent aliphatic hydrocarbon radicals containing from about 1 to about 4 carbon atoms and n is an integer from 0 to 20, and
   wherein at least one of Y and R"" is an alcohol having from about 1 to about 30 carbon atoms.

2. The lubricant additive composition of claim 1, wherein the aminoalkylphosphonic acid dialkyl ester comprises N,N-bis(2-hydroxylethyl)aminomethylphosphonic acid diethyl ester having the formula (II):

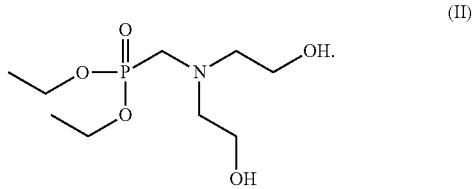 [SMILES: CCOP(=O)(CN(CCO)CCO)OCC]

3. The lubricant additive composition of claim 1, wherein the cyclized product of an aminoalkylphosphonic acid dialkyl ester comprises a cyclized product of N,N-bis(2-hydroxylethyl)aminomethylphosphonic acid diethyl ester having the formula (III):

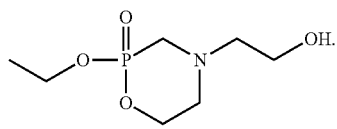
(III)

4. The lubricant additive composition of claim 1, wherein the mixture of components further comprises:
(c) a dialkyl (hydroxyalkyl)phosphonate.

5. The lubricant composition of claim 4, wherein the dialkyl (hydroxyalkyl)phosphonate comprises diethyl (hydroxymethyl)phosphonate having the formula (IV):

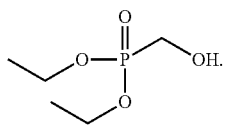
(IV)

6. The lubricant additive composition of claim 4, wherein the dialkyl (hydroxyalkyl)phosphonate is present in an amount of less than about 20 wt %, but not 0 wt %, based on the total weight percent of the additive composition.

7. The lubricant additive composition of claim 1, wherein the aminoalkylphosphonic acid dialkyl ester is present in an amount of greater than about 50 wt % based on the total weight percent of the additive composition.

8. The lubricant additive composition of claim 1, wherein the cyclized product of the aminoalkylphosphonic acid dialkyl ester is present in an amount of greater than about 20 wt % based on the total weight percent of the additive composition.

9. A composition selected from the group consisting of a lubricant composition and a hydraulic fluid composition comprising a base oil and the additive composition as defined in claim 1.

10. The composition of claim 9, wherein the additive composition is present in an amount of greater than about 0.03 wt % in the composition.

11. A method for providing antiwear protection to a lubricated surface, comprising: lubricating a surface with the composition of claim 9, wherein the antiwear protection is improved relative to a composition free of the additive composition.

12. A method for reducing friction between lubricated surfaces, comprising: lubricating a surface with the composition of claim 9, wherein friction is reduced relative to a composition free of the additive composition.

13. A process for preparing an aminoalkylphosphonic acid dialkyl ester compound, comprising
reacting together diethyl phosphite, an aldehyde, and a dialkanolamine,
wherein the aminoalkylphosphonic acid dialkyl ester compound is a compound of formula (I):

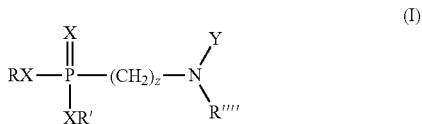
(I)

wherein each X is independently selected from sulfur and oxygen;
wherein z is 1 to 30;
wherein R and R' are independently selected from hydrocarbyl radicals containing 2 carbon atoms;
wherein Y is selected from an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20; and
wherein R"" is selected from hydrogen, an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20, and
wherein at least one of Y and R"" is an alcohol having from about 1 to about 30 carbon atoms.

14. A process for preparing an aminoalkylphosphonic acid dialkyl ester compound, comprising
reacting together a dialkyl phosphite, an aldehyde, and a dialkylamine,
wherein the dialkylamine is selected from a dipropylamine, and a dioleylamine, and
wherein the aminoalkylphosphonic acid dialkyl ester compound is a compound of formula (I):

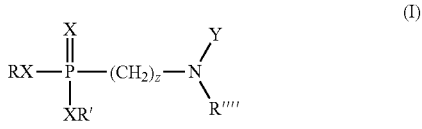
(I)

wherein each X is independently selected from sulfur and oxygen;
wherein z is 1 to 30;
wherein R and R' are independently selected from hydrocarbyl radicals containing 2 carbon atoms;
wherein Y is selected from an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20; and
wherein R"" is selected from hydrogen, an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20, and
wherein at least one of Y and R"" is an alcohol having from about 1 to about 30 carbon atoms.

15. A process for preparing an aminoalkylphosphonic acid dialkyl ester compound, comprising
   reacting together a dialkyl phosphite, an aldehyde, and bis(2-ethoxyethyl)amine,
   wherein the aminoalkylphosphonic acid dialkyl ester compound is a compound of formula (I):

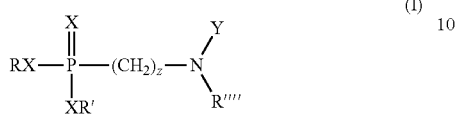

wherein each X is independently selected from sulfur and oxygen;
wherein z is 1 to 30;
wherein R and R' are independently selected from hydrocarbyl radicals containing 2 carbon atoms;
wherein Y is selected from an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20; and
wherein R"" is selected from hydrogen, an alkyl group having from about 1 to about 30 carbon atoms, an alcohol having from about 1 to about 30 carbon atoms, and the group R"O(R'"O)$_n$—H, wherein R" and R'" are independently divalent aliphatic hydrocarbon radicals containing from about 1 to about 4 carbon atoms and n is an integer from 0 to 20, and
wherein at least one of Y and R"" is an alcohol having from about 1 to about 30 carbon atoms.

16. The composition of claim 9, wherein the additive composition is present in an amount greater than about 0.05 wt % in the lubricant composition.

* * * * *

UNITED STATES PATENT AND TRADEMARK OFFICE
CERTIFICATE OF CORRECTION

PATENT NO. : 10,563,146 B2
APPLICATION NO. : 13/606208
DATED : February 18, 2020
INVENTOR(S) : Helen T. Ryan et al.

It is certified that error appears in the above-identified patent and that said Letters Patent is hereby corrected as shown below:

In the Title, please amend as follows:
--Preparation and Use of Aminoalkylphosphonic Acid Dialkyl Ester Compounds in a Lubricant for Antiwear, Friction Reduction, and/or Micropitting Prevention--

Signed and Sealed this
Eighth Day of September, 2020

Andrei Iancu
*Director of the United States Patent and Trademark Office*